United States Patent
Ramanan et al.

(10) Patent No.: US 9,504,693 B2
(45) Date of Patent: Nov. 29, 2016

(54) PHARMACEUTICAL COMPOSITIONS FOR THE TREATMENT OF CANCER AND OTHER DISEASES OR DISORDERS

(71) Applicant: Millennium Pharmaceuticals, Inc., Cambridge, MA (US)

(72) Inventors: Vijayalakshmi Ramanan, Sharon, MA (US); Irene S. Tobias, Cambridge, MA (US); Raymond D. Skwierczynski, Andover, MA (US); Dauntel S. Verwijs, Framingham, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 14/838,878

(22) Filed: Aug. 28, 2015

(65) Prior Publication Data
US 2016/0158244 A1    Jun. 9, 2016

Related U.S. Application Data

(60) Division of application No. 13/914,705, filed on Jun. 11, 2013, now Pat. No. 9,127,011, which is a continuation of application No. 12/844,920, filed on Jul. 28, 2010, now abandoned.

(60) Provisional application No. 61/230,212, filed on Jul. 31, 2009.

(51) Int. Cl.
| | |
|---|---|
| *C07D 487/04* | (2006.01) |
| *A61K 31/55* | (2006.01) |
| *A61K 9/08* | (2006.01) |
| *A61K 47/02* | (2006.01) |
| *A61K 47/10* | (2006.01) |
| *A61K 47/14* | (2006.01) |
| *A61K 47/20* | (2006.01) |
| *A61K 47/26* | (2006.01) |

(52) U.S. Cl.
CPC .......... *A61K 31/55* (2013.01); *A61K 9/08* (2013.01); *A61K 47/02* (2013.01); *A61K 47/10* (2013.01); *A61K 47/14* (2013.01); *A61K 47/20* (2013.01); *A61K 47/26* (2013.01); *C07D 487/04* (2013.01)

(58) Field of Classification Search
CPC ...... A61K 31/55; A61K 47/02; A61K 47/10; A61K 47/14; A61K 47/20; A61K 47/26; A61K 9/08; C07D 487/04
USPC ............. 514/215, 267; 544/250; 540/578
See application file for complete search history.

(56) References Cited

U.S. PATENT DOCUMENTS

| | | |
|---|---|---|
| 5,747,487 A | 5/1998 | Albright et al. |
| 6,057,329 A | 5/2000 | Davis et al. |
| 7,572,784 B2 | 8/2009 | Claiborne et al. |
| 7,718,648 B2 | 5/2010 | Claiborne et al. |
| 8,026,246 B2 | 9/2011 | Claiborne et al. |
| 9,127,011 B2 | 9/2015 | Ramanan et al. |
| 2007/0104785 A1 | 5/2007 | Navale et al. |
| 2007/0149561 A1 | 6/2007 | Dhanak et al. |
| 2007/0185087 A1 | 8/2007 | Claiborne et al. |
| 2008/0045501 A1 | 2/2008 | Claiborne et al. |
| 2008/0167292 A1 | 7/2008 | Claiborne et al. |
| 2009/0299060 A1 | 12/2009 | Claiborne et al. |
| 2010/0183601 A1 | 7/2010 | Manfredi |
| 2010/0310651 A1 | 12/2010 | Mittal |
| 2011/0039826 A1 | 2/2011 | Ramanan et al. |
| 2011/0245234 A1 | 10/2011 | Armitage et al. |
| 2011/0312942 A1 | 12/2011 | Claiborne et al. |
| 2011/0312943 A1 | 12/2011 | Claiborne et al. |
| 2014/0073630 A1 | 3/2014 | Ramanan et al. |

FOREIGN PATENT DOCUMENTS

| | | |
|---|---|---|
| WO | WO-01/10462 A1 | 2/2001 |
| WO | WO-2005/111039 A2 | 11/2005 |

(Continued)

OTHER PUBLICATIONS

Faure, A. et al., Process Control and Scale-up of Pharmaceutical Wet Granulation Processes: A Review, European Journal of Pharmaceutics and Biopharmaceutics, 52(3):269-277 (2001). Helman, J., Farmacotecnia teórica y práctica, Compañia Editorial Continental, 6(50):50.8 (1982).

(Continued)

*Primary Examiner* — Savitha Rao
(74) *Attorney, Agent, or Firm* — Choate, Hall & Stewart LLP

(57) ABSTRACT

This invention provides novel pharmaceutical compositions of the compound of formula (I):

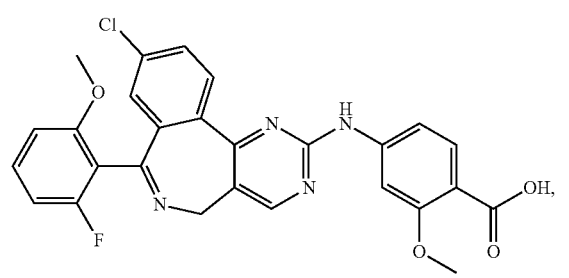

(I)

or a pharmaceutically acceptable salt thereof, that are suitable for the bulk production of an oral pharmaceutical dosage form; processes for the production of said oral pharmaceutical dosage form; and the use of the pharmaceutical composition for the treatment of patients suffering from or subject to diseases, disorders, or conditions involving cell survival, proliferation and migration, including chronic inflammatory proliferative disorders, proliferative ocular disorders, benign proliferative disorders, and cancer.

20 Claims, No Drawings

(56) References Cited

FOREIGN PATENT DOCUMENTS

| WO | WO-2008/005266 A2 | 1/2008 |
| WO | WO-2008/063525 A1 | 5/2008 |
| WO | WO-2009/070652 A1 | 6/2009 |
| WO | WO-2011/014248 A1 | 2/2011 |

OTHER PUBLICATIONS

International Search Report and Written Opinion for PCT/US2010/001434, 4 pages (Jul. 30, 2010).
International Search Report for PCT/US2009/006560, 4 pages (Jan. 3, 2010).
International Search Report for PCT/US2010/002109, 4 pages (Oct. 7, 2010).
International Search Report for PCT/US2011/024883, 2 pages (Apr. 11, 2011).
Trybulski, E.J. et al., 2-Benzazepines. 5.[1,2] Synthesis of Pyrimido [5,4-d][2]benzazepines and Their Evaluation as Anxiolytic Agents, Journal of Medicinal Chemistry, 26(11):1596-1601 (1983).
Written Opinion for PCT/US2010/002109, 5 pages (Oct. 7, 2010).
Yakushijin, Y. et al., The Expression of the Aurora-A Gene and Its Significance with Tumorgenesis in Non-Hodgkin's Lymphoma, Leukemia and Lymphoma, 45(9):1741-1746 (2004).

PHARMACEUTICAL COMPOSITIONS FOR THE TREATMENT OF CANCER AND OTHER DISEASES OR DISORDERS

PRIORITY CLAIM

This application claims priority from U.S. Provisional Patent Application Ser. No. 61/230,212, filed on Jul. 31, 2009, which is hereby incorporated by reference in its entirety.

BACKGROUND OF THE INVENTION

The present invention relates to pharmaceutical compositions of 4-{[9-chloro-7-(2-fluoro-6-methoxyphenyl)-5H-pyrimido[5,4-d][2]benzazepin-2-yl]amino}-2-methoxybenzoic acid of formula (I), or a pharmaceutically acceptable salt thereof:

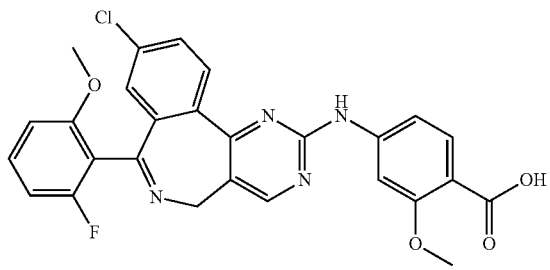

(I)

The compound of formula (I) is useful for inhibiting Aurora A kinase activity in vitro and in vivo, and is especially useful for the treatment of various cell proliferative diseases.

An example of a pharmaceutically acceptable salt of formula (I) is sodium 4-{[9-chloro-7-(2-fluoro-6-methoxyphenyl)-5H-pyrimido[5,4-d][2]benzazepin-2-yl]amino}-2-methoxybenzoate of formula (II), or a crystalline form thereof:

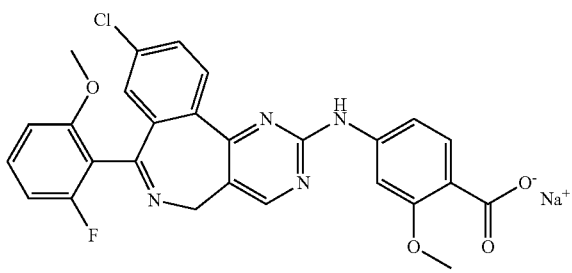

(II)

According to the American Cancer Society, an estimated 1.48 million Americans were newly-diagnosed with cancer in 2009 and about 562,000 victims died from the disease. While medical advances have improved cancer survival rates, there is a continuing need for new and more effective treatment.

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment, and cytokinesis (Dutertre et al., *Oncogene*, 21: 6175 (2002)); Berdnik et al., *Curr. Biol.*, 12: 640 (2002)). Overexpression and/or amplification of Aurora kinases have been linked to oncogenesis in several tumor types including those of colon and breast (Warner et al., *Mol. Cancer Ther.*, 2: 589 (2003); Bischoff et al., *EMBO*, 17: 3062 (1998); Sen et al., *Cancer Res.*, 94: 1320 (2002)). Moreover, Aurora kinase inhibition in tumor cells results in mitotic arrest and apoptosis, suggesting that these kinases are important targets for cancer therapy (Ditchfield, *J. Cell Biol.*, 161: 267 (2003); Harrington et al., *Nature Med.*, 1 (2004)). Given the central role of mitosis in the progression of virtually all malignancies, inhibitors of the Aurora kinases are expected to have application across a broad range of human tumors.

U.S. Pat. No. 7,572,784, US 2008/0045501, US 2008/0167292, and U.S. Application No. 61/306,047, filed Feb. 19, 2010, hereby incorporated by reference in their entirety, disclose compounds that inhibit Aurora kinase enzymes. These applications additionally disclose methods for the preparation of these compounds, pharmaceutical compositions containing these compounds, and methods for the prophylaxis and therapy of diseases, disorders, or conditions associated with overexpression and/or amplification of Aurora kinases, including, but not limited to, cell proliferative disorders such as cancer.

Sodium 4-{[9-chloro-7-(2-fluoro-6-methoxyphenyl)-5H-pyrimido[5,4-d][2]benzazepin-2-yl]amino}-2-methoxybenzoate (II) is described in WO 08/063525 and US 2008/0167292, herein incorporated by reference in their entirety.

There is a need to develop stable pharmaceutical formulations of the compound of formula (I), or a pharmaceutically acceptable salt thereof, that are convenient to administer, particularly for pediatric use.

DESCRIPTION OF THE INVENTION

In one aspect, the present invention is directed to pharmaceutical compositions of the compound of formula (I), or a pharmaceutically acceptable salt thereof, suitable for the bulk production of an oral pharmaceutical dosage form.

In another aspect, the invention provides a pharmaceutical composition of the compound of formula (I), or a pharmaceutically acceptable salt thereof, suitable for the bulk production of a liquid oral pharmaceutical dosage form.

In another aspect, the invention provides a pharmaceutical composition, comprising the compound of formula (I), or a pharmaceutically acceptable salt thereof, at least one solvent, at least one buffer, and optionally one or more pharmaceutically acceptable excipients independently selected from the group consisting of preservatives and surfactants.

In another aspect, the invention provides a process for the bulk production of the oral pharmaceutical dosage form of the compound of formula (I), or a pharmaceutically acceptable salt thereof.

In another aspect, the invention provides methods for the use of the pharmaceutical composition of the compound of formula (I), or a pharmaceutically acceptable salt thereof, for the treatment of patients suffering from or subject to diseases, disorders or conditions involving proliferative disorders including chronic inflammatory proliferative disorders, e.g., psoriasis and rheumatoid arthritis; proliferative ocular disorders, e.g., diabetic retinopathy; benign proliferative disorders, e.g., hemangiomas; and cancer.

The patent and/or scientific literature referred to herein establishes knowledge that is available to those with skill in the art. Unless otherwise defined, all technical and scientific terms used herein have the same meaning as commonly understood by one of ordinary skill in the art to which this invention relates. Although methods and materials similar or equivalent to those described herein can be used in the practice or testing of the present invention, the preferred methods and materials are described herein. The issued patents, applications, and references that are cited herein are hereby incorporated by reference to the same extent as if each was specifically and individually indicated to be incorporated by reference. In the case of inconsistencies, the present disclosure, including definitions, will control. In addition, the materials, methods, and examples are illustrative only and are not intended to be limiting.

DEFINITIONS

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

As used herein, a "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

The term "pharmaceutically acceptable excipient" is used herein to refer to a material that is compatible with a recipient subject, preferably a mammal, more preferably a human, and is suitable for delivering an active agent to the target site without terminating the activity of the agent. The toxicity or adverse effects, if any, associated with the excipient preferably are commensurate with a reasonable risk/benefit ratio for the intended use of the active ingredient. Classes of pharmaceutically acceptable excipients include, but are not limited to, surfactants, binders, disintegrants, lubricants, glidants, fillers, buffers, solvents, preservatives and taste-masking agents. For a review of pediatric oral formulations, see, e.g., Strickley R G et al., *J. Pharm. Sci.*, 97(5):1731-1774 (2007).

The term "taste-masking agent" is used herein to describe an agent that improves the palatability of a pharmaceutical composition by masking an undesirable taste or odor. Taste-masking agents include, but are not limited to, sweetening agents, flavoring agents, anti-bitter mask components, viscosity-enhancers, colors, and aroma excipients (e.g., menthol, yellow-plum-lemon aroma). Examples of sweetening agents include, but are not limited to, natural and synthetic sweeteners such as sucrose, dextrose, fructose, high fructose corn syrup, maltol, invert sugar, sorbitol, saccharin, maltitol, xylitol, saccharin sodium, sucralose, aspartame, acesulfame potassium, and cyclamates. Flavoring agents include any natural or synthetic compounds known to persons having skill in the art to impart flavors including, but not limited to, grape, cherry, berry, citrus, other fruits, mint, vanilla, chocolate, bubble gum and cinnamon. See, for example, Fenaroli's Handbook of Flavor Ingredients, 5$^{th}$ Edition, edited by George A. Burdock, Ph.D., CRC Press.

As used herein, the total weight of a single pharmaceutical dosage form, is determined by adding all the weights of the components in the pharmaceutical dosage form. The total weight of a single pharmaceutical dosage form is used as the basis for calculating the weight percentage of each of the components that comprise the pharmaceutical dosage form.

As used herein, "% w/w" is used to mean by weight as a percentage of total weight.

As used herein, "treating" or "treatment" means prevention, partial alleviation, or cure of a disease, disorder, or condition. The compounds and compositions of this invention are useful in therapeutic applications relating to an Aurora kinase-mediated disorder. As used herein, the term "Aurora kinase-mediated disorder" includes any disorder, disease or condition which is caused or characterized by an increase in Aurora kinase expression or activity, or which requires Aurora kinase activity. The term "Aurora kinase-mediated disorder" also includes any disease, disorder, or condition in which inhibition of Aurora kinase activity is beneficial. Aurora kinase-mediated disorders include proliferative disorders. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer.

As used herein, the term "Aurora kinase" refers to any one of a family of related serine/threonine kinases involved in mitotic progression. A variety of cellular proteins that play a role in cell division are substrates for phosphorylation by Aurora kinase enzymes, including, without limitation, histone H3, p 53, CENP-A, myosin II regulatory light chain, protein phosphatase-1, TPX-2, INCENP, survivin, topoisomerase II alpha, vimentin, MBD-3, MgcRacGAP, desmin, Ajuba, XIEg5 (in *Xenopus*), Ndc10p (in budding yeast), and D-TACC (in *Drosophila*). Aurora kinase enzymes also are themselves substrates for autophosphorylation, e.g., at Thr288. Unless otherwise indicated by context, the term "Aurora kinase" is meant to refer to any Aurora kinase protein from any species, including, without limitation, Aurora A, Aurora B, and Aurora C, preferably Aurora A or B. Preferably, the Aurora kinase is a human Aurora kinase.

The term "Aurora kinase inhibitor" or "inhibitor of Aurora kinase" is used to signify a compound having a structure as defined herein, which is capable of interacting with an Aurora kinase and inhibiting its enzymatic activity. Inhibiting Aurora kinase enzymatic activity means reducing the ability of an Aurora kinase to phosphorylate a substrate peptide or protein. In various embodiments, such reduction of Aurora kinase activity is at least about 50%, at least about 75%, at least about 90%, at least about 95%, or at least about 99%. In various embodiments, the concentration of Aurora kinase inhibitor required to reduce an Aurora kinase enzymatic activity is less than about 1 µM, less than about 500 nM, less than about 100 nM, or less than about 50 nM.

As used herein, "therapeutically effective amount" is meant to describe an amount of a compound, composition, medicament or other active ingredient effective in producing the desired therapeutic effect.

DETAILED DESCRIPTION OF THE INVENTION

In one embodiment, the pharmaceutical composition of the present invention comprises the compound of formula (I), or a pharmaceutically acceptable salt thereof, at least one solvent, at least one buffer, and optionally one or more pharmaceutically acceptable excipients independently selected from the group consisting of preservatives and surfactants.

In another embodiment, the pharmaceutical composition of the present invention further comprises a taste-masking agent.

In yet another embodiment, the pharmaceutical composition of the compound of formula (I), or a pharmaceutically acceptable salt thereof, is suitable for the bulk production of a liquid oral pharmaceutical dosage form. Examples of liquid oral pharmaceutical dosage forms include, but are not limited to, solutions, suspensions, and colloids.

In one embodiment, the pharmaceutical composition of the present invention comprises, about 0.05% w/w to about 5% w/w of the compound of formula (I), or a pharmaceutically acceptable salt thereof, about 50% w/w to about 99.2% w/w of solvent, about 0.01% w/w to about 30% w/w of buffer, no more than about 5% w/w of preservative, and no more than about 5% w/w of surfactant. In another embodiment, the pharmaceutical composition comprises, about 0.05% w/w to about 5% w/w of the compound of formula (I), or a pharmaceutically acceptable salt thereof, about 50% w/w to about 99% w/w of solvent, about 0.01% w/w to about 30% w/w of buffer, no more than about 60% w/w of taste-masking agent, no more than about 5% w/w of preservative, and no more than about 5% w/w of surfactant. In still another embodiment, the pharmaceutical composition comprises; about 0.10% w/w to about 2% w/w of the compound of formula (I), or a pharmaceutically acceptable salt thereof, about 65% w/w to about 99% w/w of solvent, about 0.20% w/w to about 3% w/w of buffer, and about 15% w/w to about 50% w/w of taste-masking agent.

In another embodiment, the pharmaceutical composition comprises, about 0.44% w/w of the compound of formula (I), or a pharmaceutically acceptable salt thereof, about 99.14% w/w of solvent, and about 0.42% w/w of buffer.

In another embodiment, the pharmaceutical composition comprises, about 0.47% w/w of the compound of formula (II), or a crystalline form thereof, about 77.36% w/w of solvent, about 21.75% w/w of taste-masking agent, and about 0.42% w/w of buffer.

In another embodiment, the pharmaceutical composition comprises, about 0.47% w/w of the compound of formula (II), or a crystalline form thereof, about 98.41% w/w of solvent, about 0.7% w/w of taste-masking agent, and about 0.42% w/w of buffer.

In another embodiment, the pharmaceutical composition comprises, about 0.47% w/w of the compound of formula (II), or a crystalline form thereof, about 78.11 w/w of solvent, about 21% w/w of taste-masking agent, and about 0.42% w/w of buffer.

In one embodiment, the pharmaceutical composition of the present invention is a liquid oral pharmaceutical dosage form. In another embodiment, the pharmaceutical composition dosage form is for pediatric dosing. In another embodiment, the pharmaceutical composition dosage form is for dosing adults.

In some embodiments, the pharmaceutical composition of the present invention comprises a salt of the compound of formula (I), preferably the sodium salt of formula (II), or a crystalline form thereof.

Using the analytical method described in Example 9, the amount of the compound of formula (I), or a pharmaceutically acceptable salt thereof, present in the test sample may be measured by comparison to a reference standard of the compound of formula (II), or a crystalline form thereof. Based on a 1:1 molecular ratio for the conversion of the compound of formula (I) to the compound of formula (II), a molecular weight conversion gives the amount of the compound of formula (I) present in the test sample.

In some embodiments, the amount of the compound of formula (I), or a pharmaceutically acceptable salt thereof, present in a pharmaceutical composition is expressed as the equivalent amount of the compound of formula (II), based on the relative molecular weights of the compound of formula (I) and the compound of formula (II). For example, in some embodiments, the pharmaceutical composition comprises 0.47% w/w of the compound formula (II), which is equivalent to 0.44% w/w of the compound formula (I) taking into account the molecular weight conversion.

In some embodiments, the pharmaceutical composition comprises a compound of formula (I) or a compound of formula (II), which is present in an amount of about 0.05% w/w to about 5% w/w. In some other embodiments, the compound of formula (I) or the compound of formula (II) is present in an amount of about 0.10% w/w to about 2% w/w. In yet some other embodiments, the compound of formula (I) or the compound of formula (II) is present in an amount of about 0.10% w/w, or about 0.20% w/w, or about 0.30% w/w, or about 0.40% w/w, or about 0.50% w/w, or about 1.0% w/w, or about 1.5% w/w, or about 2.0% w/w, or about 2.5% w/w, or about 3.0% w/w, or about 3.5% w/w, or about 4.0% w/w, or about 4.5% w/w, or about 5.0% w/w. In yet some other embodiments, the compound of formula (I) or the compound of formula (II) is present in an amount of about 0.10% w/w, or about 0.15% w/w, or about 0.20% w/w, 0.25% w/w, or about 0.30% w/w, or about 0.35% w/w, or about 0.40% w/w, or about 0.45% w/w, or about 0.50% w/w, or about 0.55% w/w, or about 0.60% w/w, or about 0.65% w/w, or about 0.70% w/w, or about 0.75% w/w, or about 0.80% w/w, or about 0.85% w/w, or about 0.90% w/w, or about 0.95% w/w, or about 1.0% w/w, or about 1.05% w/w, or about 1.10% w/w, or about 1.15% w/w, or about 1.20% w/w, or about 1.25%0 w/w, or about 1.30% w/w, or about 1.35% w/w, or about 1.40% w/w, or about 1.45% w/w, or about 1.50% w/w, or about 1.55% w/w, or about 1.60% w/w, or about 1.65% w/w, or about 1.70% w/w, or about 1.75% w/w, or about 1.80% w/w, or about 1.85% w/w, or about 1.90% w/w, or about 1.95% w/w, or about 2.0% w/w. In yet some other embodiments, the compound of formula (I) or the compound of formula (II) is present in an amount of about 0.40% w/w to about 0.50% w/w. In yet some other embodiments, the compound of formula (I) or the compound of formula (II) is present in an amount of about 0.21% w/w, or about 0.22% w/w, or about 0.23% w/w, or about 0.24% w/w, or about 0.25% w/w, or about 0.26% w/w, or about 0.27% w/w, or about 0.28% w/w, or about 0.29% w/w, or about 0.30% w/w, or about 0.31% w/w, or about 0.32% w/w, or about 0.33% w/w, or about 0.34% w/w, or about 0.35% w/w, or about 0.36% w/w, or about 0.37% w/w, or about 0.38% w/w, or about 0.39% w/w, or about 0.40% w/w, or about 0.41% w/w, or about 0.42% w/w, or about 0.43% w/w, or about 0.44% w/w, or about 0.45% w/w, or about 0.46% w/w, or about 0.47% w/w, or about 0.48% w/w, or about 0.49% w/w.

In some embodiments, the pharmaceutical composition comprises solvent present in an amount of about 50% w/w to about 99.2% w/w. In some other embodiments, the pharmaceutical composition comprises solvent present in an amount of about 65% w/w to about 99% w/w. In some other embodiments, the pharmaceutical composition comprises solvent present in an amount of about 75% w/w to about 99% w/w. In still other embodiments, the pharmaceutical composition comprises solvent present in an amount of about 65% w/w, or about 66% w/w, or about 67% w/w, or about 68% w/w, or about 69% w/w, or about 70% w/w, or about 71% w/w, or about 72% w/w, or about 73% w/w, or about 74% w/w, or about 75% w/w, or about 76% w/w, or about 77% w/w, or about 78% w/w, or about 79% w/w, or about 80% w/w, or about 81% w/w, or about 82% w/w, or about 83% w/w, or about 84% w/w, or about 85% w/w, or about 86% w/w, or about 87% w/w, or about 88% w/w, or about 89% w/w, or about 90% w/w, or about 91% w/w, or about 92% w/w, or about 93% w/w, or about 94% w/w, or about 95% w/w, or about 96% w/w, or about 97% w/w, or about 98% w/w, or about 99% w/w. In yet other embodiments, the pharmaceutical composition comprises solvent present in an amount of about 99.11% w/w, or about 99.12% w/w, or about 99.13% w/w, or about 99.14% w/w, or about 99.15% w/w, or about 99.16% w/w, or about 99.17% w/w, or about 99.18% w/w, or about 99.19% w/w, or about 99.2% w/w. In yet other embodiments, the pharmaceutical composition comprises solvent present in an amount of about 77.65 w/w, or about 77.66% w/w, or about 77.67% w/w, or about 77.68% w/w, or about 77.69% w/w, or about 77.70% w/w, or about 77.71% w/w, or about 77.72% w/w, or about 77.73% w/w, or about 77.74% w/w, or about 77.75% w/w.

Suitable solvents include, but are not limited to, propylene glycol, glycerin, polyethylene glycol (PEG400), polyethylene glycol (PEG3350), ethanol, cyclodextrins (e.g., hydroxypropyl beta cyclodextrin (HPBCD)), vegetable oils, castor oil, medium-chain tryglycerides, purified water and mixtures thereof. In one embodiment, the solvent is a mixture of PEG400, propylene glycol, and purified water.

In some embodiments, the pharmaceutical composition comprises buffer present in an amount of no more than about 30% w/w. In some other embodiments, the pharmaceutical composition comprises buffer present in an amount of about 0.20 w/w to about 3% w/w. In still other embodiments, the pharmaceutical composition comprises buffer present in an amount of about 1.0% w/w, or about 1.5% w/w, or about 2.0% w/w, or about 2.5% w/w, or about 3.0% w/w, or about 3.5% w/w, or about 4.0% w/w, or about 4.5% w/w, or about 5.0% w/w, or about 5.5% w/w, or about 6.0% w/w, or about 6.5% w/w, or about 7.0% w/w, or about 7.5% w/w, or about 8.0% w/w, or about 8.5% w/w, or about 9.0% w/w, or about 9.5% w/w, or about 10.0% w/w. In still other embodiments, the pharmaceutical composition comprises buffer present in an amount of or about 15% w/w, or about 20% w/w, or about 25% w/w, or about 30% w/w. In still other embodiments, the pharmaceutical composition comprises buffer present in an amount of about 0.01% w/w, or about 0.05 w/w, or about 0.10% w/w, or about 0.15% w/w, or about 0.20% w/w, or about 0.25% w/w, or about 0.30% w/w, or about 0.35% w/w, or about 0.40% w/w, or about 0.45 w/w, or about 0.50% w/w, or about 0.55% w/w, or about 0.60% w/w, or about 0.65 w/w, or about 0.70% w/w, or about 0.75% w/w, or about 0.80% w/w, or about 0.85% w/w, or about 0.90% w/w, or about 0.95% w/w. In still other embodiments, the pharmaceutical composition comprises buffer present in an amount of about 0.41% w/w, or about 0.42% w/w, or about 0.43% w/w, or about 0.44% w/w.

Suitable buffers include, but are not limited to, sodium bicarbonate, disodium phosphate, dipotassium phosphate, potassium bicarbonate, sodium carbonate, potassium carbonate, and mixtures thereof. In one embodiment, the buffer is sodium bicarbonate.

In some embodiments, the pharmaceutical composition optionally comprises a preservative, which may be present in an amount of no more than about 5% w/w. In some other embodiments, the preservative is present in an amount of no more than about 2% w/w. In some other embodiments, the preservative is present in an amount of no more than about 1% w/w. In some other embodiments, the preservative is present in an amount of about 0.5% w/w, or about 1.0% w/w, or about 1.5% w/w, or about 2.0% w/w, or about 2.5 w/w, or about 3.0% w/w, or about 3.5% w/w, or about 4.0% w/w, or about 4.5% w/w, or about 5.0% w/w. In still other embodiments, the pharmaceutical composition comprises a preservative present in an amount of about 0.01% w/w, or about 0.05% w/w, or about 0.10% w/w, or about 0.15% w/w, or about 0.20% w/w, or about 0.25% w/w, or about 0.30% w/w, or about 0.35% w/w, or about 0.40% w/w, or about 0.45% w/w, or about 0.50% w/w, or about 0.55% w/w, or about 0.60% w/w, or about 0.65% w/w, or about 0.70% w/w, or about 0.75% w/w, or about 0.80% w/w, or about 0.85% w/w, or about 0.90% w/w, or about 0.95% w/w.

Suitable preservatives include, but are not limited to, parabens, such as methylparaben, ethylparaben, propylparaben, butylparaben, isobutylparaben, isopropylparaben, benzylparaben and their sodium salts, butylated hydroxy anisole, butylated hydroxy toluene, EDTA, formaldehyde-generating derivatives, sodium benzoate, potassium sorbate, and mixtures thereof. In one embodiment, the preservative is a mixture of methylparaben and propylparaben.

In some embodiments, the pharmaceutical composition optionally comprises a surfactant, which may be present in an amount of no more than about 5% w/w. In some other embodiments, the surfactant is present in an amount of no more than about 2 w/w. In some other embodiments, the surfactant is present in an amount of no more than about 1% w/w. In some embodiments, the surfactant is present in an amount of about 0.5% w/w, or about 1.0% w/w, or about 1.5% w/w, or about 2.0 w/w, or about 2.5% w/w, or about 3.0% w/w, or about 3.5% w/w, or about 4.0% w/w, or about 4.5% w/w, or about 5.0% w/w. In still other embodiments, the pharmaceutical composition comprises surfactant present in an amount of about 0.01% w/w, or about 0.05% w/w, or about 0.10% w/w, or about 0.15% w/w, or about 0.20% w/w, or about 0.25% w/w, or about 0.30% w/w, or about 0.35% w/w, or about 0.40% w/w, or about 0.45% w/w, or about 0.50% w/w, or about 0.55% w/w, or about 0.60% w/w, or about 0.65% w/w, or about 0.70% w/w, or about 0.75% w/w, or about 0.80% w/w, or about 0.85% w/w, or about 0.90% w/w, or about 0.95% w/w.

Suitable surfactants include, but are not limited to, sodium lauryl sulfate, sodium dodecyl sulfate, polysorbates (e.g., Tween 20 and Tween 80), poloxamers (e.g., Poloxamer 331 and Poloxamer 407), glyceryl monooleate, and mixtures thereof. In one embodiment, the surfactant is sodium lauryl sulfate.

In some embodiments, the pharmaceutical composition optionally comprises a taste-masking agent, which may be present in an amount of no more than about 60% w/w. In some other embodiments, the taste-masking agent is present in an amount of about 15% w/w to about 50% w/w. In some other embodiments, the taste-masking agent is present in an amount of about 0.05% w/w, or about 0.10% w/w, or about 0.15 w/w, or about 0.20% w/w, or about 0.25% w/w, or about 0.50% w/w, or about 0.60% w/w, or about 0.70% w/w, or about 0.80% w/w, or about 0.90% w/w, or about 1% w/w, or about 2% w/w, or about 3% w/w, or about 4% w/w, or about 5% w/w, or about 10% w/w, or about 15% w/w, or about 20% w/w, or about 25% w/w, or about 30% w/w, or about 35% w/w, or about 40% w/w, or about 45% w/w, or about 50% w/w, or about 55% w/w, or about 60% w/w. In still other embodiments, the pharmaceutical composition optionally comprises a taste-masking agent present in an amount of about 21% w/w, or about 22% w/w, or about 23% w/w, or about 24% w/w, or about 25% w/w, or about 26% w/w, or about 27% w/w, or about 28% w/w, or about 29% w/w, or about 30% w/w, or about 31% w/w, or about 32% w/w, or about 33% w/w, or about 34% w/w, or about 35% w/w, or about 36% w/w, or about 37% w/w, or about 38% w/w, or about 39% w/w.

In some embodiments, the taste-masking agent comprises a sweetener. Suitable sweeteners include, but are not limited to, sucrose, dextrose, fructose, high fructose corn syrup, maltol, invert sugar, sorbitol, saccharin, maltitol, xylitol, saccharin sodium, sucralose, aspartame, acesulfame potassium, and cyclamates and mixtures thereof. Sweeteners may be added to the formulation in the form of solutions in water, e.g., a 70% solution of sorbitol in water, or syrups, e.g., Lycasin®. In one embodiment, the sweetener is sorbitol. In another embodiment, the sweetener is acesulfame potassium. In still another embodiment, the sweetener is a mixture of sorbitol and acesulfame potassium.

In some embodiments, the taste-masking agent comprises a flavoring agent. Suitable flavoring agents include, but are not limited to, artificial flavor systems such as, strawberry, orange, mixed berry or bubblegum (Ungerer & Co., Lincoln Park, N.J.).

In some embodiments, the pharmaceutical composition of the present invention comprises an anti-foaming agent. Suitable anti-foaming agents include, but are not limited to, simethicone, dimethicone and mixtures thereof.

In one embodiment, the pharmaceutical composition of the present invention comprises, the compound of formula (I), propylene glycol, sodium bicarbonate, and purified water.

In another embodiment, the pharmaceutical composition of the present invention comprises, the compound of formula (I), propylene glycol, PEG 400, sodium bicarbonate, and purified water.

In still another embodiment, the pharmaceutical composition of the present invention comprises, the compound of formula (I), propylene glycol, sodium bicarbonate, sodium lauryl sulfate, and purified water.

In still another embodiment, the pharmaceutical composition of the present invention comprises, the compound of formula (I), propylene glycol, sodium bicarbonate, sodium lauryl sulfate, methylparaben, propylparaben, and purified water.

In still another embodiment, the pharmaceutical composition of the present invention comprises, the compound of formula (I), propylene glycol, sodium bicarbonate, glycerin, methylparaben, propylparaben, and purified water.

In still another embodiment, the pharmaceutical composition of the present invention comprises, the compound of formula (I), propylene glycol, PEG 400, sodium bicarbonate, glycerin, and purified water.

In yet another embodiment, the pharmaceutical composition of the present invention comprises, the compound of formula (I), propylene glycol, sodium bicarbonate, a taste-masking agent, and purified water.

In another embodiment, the pharmaceutical composition of the present invention comprises, the compound of formula (I), propylene glycol, PEG 400, sodium bicarbonate, a taste-masking agent, and purified water.

In still another embodiment, the pharmaceutical composition of the present invention comprises, the compound of formula (I), propylene glycol, sodium bicarbonate, sodium lauryl sulfate, a taste-masking agent, and purified water.

In still another embodiment, the pharmaceutical composition of the present invention comprises, the compound of formula (I), propylene glycol, sodium bicarbonate, sodium lauryl sulfate, methylparaben, propylparaben, a taste-masking agent, and purified water.

In still another embodiment, the pharmaceutical composition of the present invention comprises, the compound of formula (I), propylene glycol, sodium bicarbonate, glycerin, methylparaben, propylparaben, a taste-masking agent, and purified water.

In still another embodiment, the pharmaceutical composition of the present invention comprises, the compound of formula (I), propylene glycol, PEG 400, sodium bicarbonate, glycerin, a taste-masking agent, and purified water.

One embodiment of the invention is directed to a unit dose pharmaceutical composition comprising about 0.05 mg/mL to about 25 mg/mL of or a pharmaceutically acceptable salt thereof. In another embodiment, the unit dose pharmaceutical composition comprises about 0.1 mg/mL to about 3 mg/mL of the compound of formula (I), or a pharmaceutically acceptable salt thereof.

In some embodiments, the invention provides a process for the bulk production of an oral liquid pharmaceutical dosage form of the compound of formula (I), or a pharmaceutically acceptable salt thereof, comprising the steps of:

(a-1) dissolving the compound of formula (I), or a pharmaceutically acceptable salt thereof, into a mixture comprising at least one solvent, at least one buffer, and optionally one or more taste-masking agents;

(a-2) filtering the resulting solution from (a-1) through a suitably sized filter; and (a-3) filling the filtered solution resulting from (a-2) into suitable bottles.

In some embodiments, the invention provides a process for the bulk production of an oral liquid pharmaceutical dosage form of the compound of formula (I), or a pharmaceutically acceptable salt thereof, comprising the steps of:

(a-1) dissolving the compound of formula (I), or a pharmaceutically acceptable salt thereof, into a mixture comprising at least one solvent, at least one taste-masking agent, and at least one buffer;

(a-2) filtering the resulting solution from (a-1) through a suitably sized filter; and (a-3) filling the filtered solution resulting from (a-2) into suitable bottles.

In some other embodiments, the invention provides a process for the bulk production of an oral liquid pharmaceutical dosage form of the compound of formula (I), or a pharmaceutically acceptable salt thereof, comprising the steps of:

(a-1) dissolving the compound of formula (I), or a pharmaceutically acceptable salt thereof, into a mixture comprising propylene glycol, purified water, PEG400, sorbitol, acesulfame potassium, and sodium bicarbonate;

(a-2) filtering the resulting solution from (a-1) through a suitably sized filter; and (a-3) filling the filtered solution resulting from (a-2) into suitable bottles.

In some embodiments, the compound of formula (I) of step (a-1) is a pharmaceutically acceptable salt of the compound of formula (I). If pharmaceutically acceptable salts of the compound of formula (I) are utilized in preparing the compositions of the invention, the salts preferably are base addition salts.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

In some embodiments, the active ingredient of step (a-1) is a compound of formula (I), or a sodium or potassium salt thereof. In some embodiments, the active ingredient of step (a-1) is the sodium salt of formula (II), or a crystalline form thereof.

In some embodiments, the active ingredient of step (a-1) is a crystalline form of the compound of formula (I). In some other embodiments, the active ingredient of step (a-1) is a crystalline form of a pharmaceutically acceptable salt of the compound of formula (I). Some examples of pharmaceutically acceptable salts of the compound of formula (I) and crystalline forms thereof can be found in U.S. Pat. No. 7,572,784, US Publication No. 2008/0167292, and U.S. Application No. 61/306,047, filed Feb. 19, 2010, hereby incorporated by reference in their entirety. In some embodiments, the active ingredient of step (a-1) is a polymorph of the sodium salt of formula (II), for example form 1 or form 2, as described in WO 08/063525 and US 2008/0167292, herein incorporated by reference in their entirety.

The process steps outlined above employ conventional apparatus or equipment. The dissolving step (a-1) outlined herein can take place in any conventional apparatus or equipment. Examples of such equipment include, but are not limited to, overhead mixers such as IKA® Mixers, and LIGHTNIN Stainless Steel Enhanced classic Line (ECL) portable mixers.

The filtering step (a-2) outlined herein can take place in any conventional apparatus or equipment. Examples of such equipment include, but are not limited to, 10 KM polypropylene filters, and nylon filters.

The filling step (a-3) outlined herein can take place using any conventional apparatus or equipment. One skilled in the art would be able to select a bottle suitable to hold a desired quantity of the pharmaceutical composition and provide stable storage conditions. Examples of suitable bottles include, but are not limited to, USP Type I borosilicate glass bottles, USP Type III soda-lime glass bottles, and polyethylene terephthalate (PETE) plastic bottles. The aforementioned bottles may be fitted with a suitably sized cap, which may optionally be child resistant. Examples of suitable caps include, but are not limited to, 20-400 or 24-400 polypropylene caps. In some embodiments, the aforementioned caps have liners, e.g., F217 foamed polyethylene liners or TRI-Foil® WP F-217 liners (Tri-Seal Holdings Inc., Blauvelt, N.Y.). It will be understood by one skilled in the art that the cap size may change according to the bottle size.

In some embodiments, the pharmaceutical compositions of the present invention may be administered via dose delivery devices including, but not limited to, spoons, droppers, measuring cups, cylindrical measuring scoops, graduated pipettes, and oral syringes, which may optionally be pre-filled with the pharmaceutical compositions of the present invention.

The pharmaceutical compositions, according to the method of the present invention, may be administered using any amount effective for treating the disease. The exact amount required will vary from subject to subject, depending on the species, age, and general condition of the subject, the severity of the infection, the particular agent, its mode of administration, and the like. The pharmaceutical compositions are preferably formulated in an oral pharmaceutical dosage form for ease of administration and uniformity of dosage. The expression "unit dosage form" as used herein refers to a physically discrete unit of agent appropriate for the subject to be treated. It will be understood, however, that the total daily usage of the pharmaceutical compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human. In certain embodiments, the compounds of the invention may be administered orally at total dosage levels of about 1.0 mg/kg to about 7.0 mg/kg and preferably from about 1.4 mg/kg to about 6.2 mg/kg, of subject body weight per day, administered in one or more doses during the day, to obtain the desired therapeutic effect.

The physical and chemical stability of the oral pharmaceutical dosage form may be tested in a conventional manner, for example, by appearance, or assay for the compound of formula (I), or a pharmaceutically acceptable salt thereof, degradation products, after storage at different temperatures for different lengths of time.

The pharmacological properties of the pharmaceutical composition is such that it is suitable for use in the treatment of patients suffering from or subject to diseases, disorders or conditions mediated by Aurora kinases, in particular Aurora A or B. Inhibiting Aurora kinase activity, in particular Aurora A or B, may serve to treat a number of diseases involving cell survival, proliferation and migration, including chronic inflammatory proliferative disorders, e.g., psoriasis and rheumatoid arthritis; proliferative ocular disorders, e.g., diabetic retinopathy; benign proliferative disorders, e.g., hemangiomas; and cancer.

In another aspect, the invention pertains to a method for treating cancer, comprising the administration of a therapeutically effective amount of the pharmaceutical composition of the present invention to a subject in need thereof. In some embodiments, the cancer is a solid tumor. Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), refractory anemia with excess blasts (RAEB), and RAEB in transformation (RAEB-T); and myeloproliferative syndromes.

In still other embodiments, the cancer is selected from the group consisting of colorectal cancer, ovarian cancer, breast cancer, gastric cancer, prostate cancer, and pancreatic cancer. In still other embodiments, the cancer is selected from the group consisting of neuroblastoma or ALL. In certain particular embodiments, the cancer is pediatric neuroblastoma or pediatric ALL.

The pharmaceutical composition may be used in an application of monotherapy to treat a disorder, disease or symptom, it also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the pharmaceutical composition of the invention is used in combination with other therapeutic agents, such as other inhibitors of kinases, especially serine/threonine kinases. In some embodiments, the pharmaceutical composition of the invention is administered in conjunction with a therapeutic agent selected from the group consisting of cytotoxic agents, radiotherapy, and immunotherapy. It is understood that other combinations may be undertaken while remaining within the scope of the invention.

In order that this invention be more fully understood, the following preparative examples are set forth. These examples illustrate how to make or test specific compositions, and are not to be construed as limiting the scope of the invention in any way.

EXAMPLES

Sodium 4-{[9-chloro-7-(2-fluoro-6-methoxyphenyl)-5H-pyrimido[5,4-d][2]benzazepin-2-yl]amino}-2-methoxybenzoate polymorph form 1 or form 2 of formula (II) may be prepared according to synthetic methods described in WO 08/063525 and U.S. Ser. No. 08/016,7292, hereby incorporated by reference in their entirety. While sodium 4-{[9-chloro-7-(2-fluoro-6-methoxyphenyl)-5H-pyrimido [5,4-d][2]benzazepin-2-yl]amino}-2-methoxybenzoate polymorph form 2 of formula (II) was used in the examples described herein, it will be understood that polymorph form 1 of formula (II), or any polymorph form of formula (II) may be used to prepare the pharmaceutical composition of the present invention. Further examples of polymorphs of formula (II) may be found in U.S. Application No. 61/306,047, filed Feb. 19, 2010, hereby incorporated by reference in its entirety.

Example 1

A 25.0 kg batch was manufactured by the following process Sodium 4-{[9-chloro-7-(2-fluoro-6-methoxyphenyl)-5H -pyrimido[5,4-d][2]benzazepin-2-yl]amino}-2-methoxybenzoate polymorph form 2 of formula (II) (0.119 kg) was screened and solubilized with polyethylene glycol 400 (7.5 kg) and propylene glycol (7.5 kg) to provide mixture #1 using an IKA mixer model RW-20 with a stainless steel marine -type propeller. Sodium bicarbonate (0.105 kg), sorbitol 70% solution in water (7.5 kg) and purified water (2.285 kg) were mixed separately to provide mixture #2 using an IKA mixer model RW-20 with a stainless steel marine-type propeller. In the final mixing step, mixtures #1 and #2 were mixed together to provide a homogenous solution using an IKA mixer model RW-20 with a stainless steel marine-type propeller. This solution was then filtered through a 10 µM polypropylene filter and was stored in 4 L amber glass jugs having a PTFE liner for bulk storage. The bulk solution was then dispensed into 20 mL USP Type I borosilicate amber glass bottles with 20-400 white polypropylene caps having a F217 foamed polyethylene liner. The batch composition is shown in Table 1.

TABLE 1

Pharmaceutical composition

| Material | Function | Composition (% w/w) |
|---|---|---|
| Compound of formula (II) | Drug Substance | 0.47 |
| Polyethylene Glycol 400 | Solvent | 30.0 |
| Sorbitol (added as a 70% solution in water) | Taste-masking Agent | 30.0 |
| Propylene Glycol | Solvent | 30.0 |
| Sodium Bicarbonate | Buffer | 0.42 |
| Purified Water | Solvent | 9.11 |

Example 2

The pharmaceutical composition shown below in Table 2 was prepared using procedures generally similar to those described in Example 1.

TABLE 2

Pharmaceutical composition

| Material | Function | Composition (% w/w) |
|---|---|---|
| Compound of formula (II) | Drug Substance | 0.47 |
| Propylene Glycol | Solvent | 50.0 |
| Sodium Bicarbonate | Buffer | 0.42 |
| Sodium Lauryl Sulfate | Surfactant | 0.50 |
| Methylparaben | Preservative | 0.18 |
| Propylparaben | Preservative | 0.02 |
| Purified Water | Solvent | 48.41 |

Example 3

The pharmaceutical composition shown below in Table 3 was prepared using procedures generally similar to those described in Example 1.

TABLE 3

Pharmaceutical composition

| Material | Function | Composition (% w/w) |
|---|---|---|
| Compound of formula (II) | Drug Substance | 0.47 |
| Glycerin | Solvent | 30.0 |

TABLE 3-continued

Pharmaceutical composition

| Material | Function | Composition (% w/w) |
|---|---|---|
| Propylene Glycol | Solvent | 30.0 |
| Sodium Bicarbonate | Buffer | 0.42 |
| Sorbitol (added as a 70% solution in water) | Taste-masking Agent | 30.0 |
| Methylparaben | Preservative | 0.18 |
| Propylparaben | Preservative | 0.02 |
| Purified Water | Solvent | 8.91 |

Example 4

The pharmaceutical composition shown below in Table 4 was prepared using procedures generally similar to those described in Example 1.

TABLE 4

Pharmaceutical composition

| Material | Function | Composition (% w/w) |
|---|---|---|
| Compound of formula (II) | Drug Substance | 0.47 |
| Propylene Glycol | Solvent | 50.0 |
| Sodium Lauryl Sulfate | Surfactant | 0.50 |
| Sodium Bicarbonate | Buffer | 0.42 |
| Maltitol | Taste-masking Agent | 30.0 |
| Methylparaben | Preservative | 0.18 |
| Propylparaben | Preservative | 0.02 |
| Purified Water | Solvent | 18.41 |

Example 5

The pharmaceutical composition shown below in Table 5 was prepared using procedures generally similar to those described in Example 1.

TABLE 5

Pharmaceutical composition

| Material | Function | Composition (% w/w) |
|---|---|---|
| Compound of formula (II) | Drug Substance | 0.47 |
| Propylene Glycol | Solvent | 50.0 |
| Sodium Lauryl Sulfate | Surfactant | 0.50 |
| Sodium Bicarbonate | Buffer | 0.42 |
| Xylitol | Taste-masking Agent | 30.0 |
| Methylparaben | Preservative | 0.18 |
| Propylparaben | Preservative | 0.02 |
| Purified Water | Solvent | 18.41 |

Example 6

The pharmaceutical composition shown below in Table 6 was prepared using procedures generally similar to those described in Example 1.

TABLE 6

Pharmaceutical composition

| Material | Function | Composition (% w/w) |
|---|---|---|
| Compound of formula (II) | Drug Substance | 0.47 |
| Propylene Glycol | Solvent | 15.0 |
| Glycerin | Solvent | 30.0 |
| Sodium Bicarbonate | Buffer | 0.42 |
| Polyethylene Glycol 400 | Solvent | 15.0 |
| Acesulfame Potassium | Taste-masking Agent | 0.70 |
| Purified Water | Solvent | 38.41 |

Example 7

The pharmaceutical composition shown below in Table 7 was prepared using procedures generally similar to those described in Example 1.

TABLE 7

Pharmaceutical composition

| Material | Function | Composition (% w/w) |
|---|---|---|
| Compound of formula (II) | Drug Substance | 0.47 |
| Propylene Glycol | Solvent | 15.0 |
| Glycerin | Solvent | 30.0 |
| Sodium Bicarbonate | Buffer | 0.42 |
| Polyethylene Glycol 400 | Solvent | 15.0 |
| Sorbitol | Taste-masking Agent | 20.0 |
| Purified Water | Solvent | 19.11 |

Example 8

The pharmaceutical composition shown below in Table 8 was prepared using procedures generally similar to those described in Example 1.

TABLE 8

Pharmaceutical composition

| Material | Function | Composition (% w/w) |
|---|---|---|
| Compound of formula (II) | Drug Substance | 0.47 |
| Propylene Glycol | Solvent | 15.0 |
| Glycerin | Solvent | 30.0 |
| Sodium Bicarbonate | Buffer | 0.42 |
| Polyethylene Glycol 400 | Solvent | 15.0 |
| Sorbitol | Taste-masking Agent | 21.0 |
| Acesulfame Potassium | Taste-masking Agent | 0.40 |
| Artificial Bubblegum Flavor | Taste-masking Agent | 0.35 |
| Purified Water | Solvent | 17.36 |

Example 9

Analytical Method

Reversed-phase HPLC using a C18 column at ambient temperature with ultraviolet (UV) detection at 312 nm.

Mobile Phase: The gradient starts at 75% mobile phase A (0.1% triflouroacetic acid in water) and 25% mobile phase B (0.1% triflouroacetic acid in acetonitrile) and ends in 15% mobile phase A after 42 minutes.

The test sample is prepared by dissolving an aliquot of the pharmaceutical composition in diluent, which is 50:50 (v/v) acetonitrile:water. The presence of the compound of formula (I) in the test sample is confirmed by comparison of the sample retention time to that of a reference standard. The reference standard employed is a known amount of the compound of formula (II), of known purity. The reference standard is prepared by dissolving the compound of formula (II) in 50:50 (v/v) acetonitrile:water. The amount of the compound of formula (I) present in the sample is calculated from area under the peak, on a weight-to-weight comparison including a molecular weight conversion, with the area under the peak of the reference standard. The molecular weight conversion accounts for the molecular weight ratio of formula (I) to formula (II). Alternatively, the reference standard employed may be a known amount of the compound of formula (I), of known purity, which may be prepared under the same conditions as the reference standard of the compound of formula (II). The limit of quantitation for the method is 0.05% and the calculated limit of detection is 0.02%.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A method for treating Aurora A kinase mediated cancer, comprising the administration of a therapeutically effective amount of a liquid pharmaceutical composition comprising a sodium salt of formula (II):

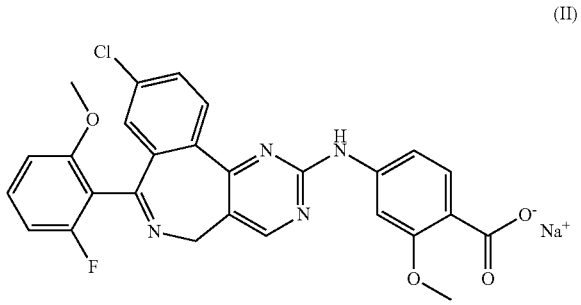 [SMILES: COc1cc(Nc2ncc3c(n2)-c2ccc(Cl)cc2C(c2c(F)cccc2OC)=NC3)ccc1C(=O)[O-] ; [Na+]]

(II)

or a crystalline form thereof, wherein the pharmaceutical composition comprises about 0.10% w/w to about 2% w/w of the compound of formula (II), or a crystalline form thereof; about 0.20% to about 3% w/w of buffer, wherein the buffer is sodium bicarbonate; and a solvent mixture of propylene glycol, purified water, PEG400, and optionally glycerin; wherein the solvent contains less than about 50% purified water, and the composition contains at least about 15% w/w propylene glycol and at least about 15% w/w PEG400.

2. The method of claim 1, wherein the cancer is colorectal cancer, lung cancer, ovarian cancer, breast cancer, gastric cancer, prostate cancer, pancreatic cancer, neuroblastoma, or acute lymphoblastic leukemia.

3. The method of claim 2, wherein the cancer is lung cancer.

4. The method of claim 1, wherein the compound of formula (II) is present in an amount of about 0.40% w/w to about 0.50% w/w.

5. The method of claim 1, wherein the solvent is a mixture of propylene glycol, glycerin, PEG400, and purified water.

6. The method of claim 1, wherein the sodium bicarbonate is present in an amount of about 0.42% w/w.

7. The method of claim 1, wherein the pharmaceutical composition further comprises a surfactant present in an amount of no more than about 1% w/w, wherein the surfactant is sodium lauryl sulfate.

8. The method of claim 7, wherein the surfactant is present in an amount of about 0.5% w/w.

9. The method of claim 1, wherein the pharmaceutical composition further comprises a taste-masking agent, wherein the taste-masking agent is selected from the group consisting of sorbitol, maltitol, sucrose, acesulfame potassium and mixtures thereof.

10. The method of claim 9, wherein the taste-masking agent is sorbitol or acesulfame potassium.

11. The method of claim 1, wherein the solvent is present in an amount of about 97%, or about 98%, or about 99% w/w.

12. The method of claim 1, wherein the solvent is present in an amount of about 68%, or about 69%, or about 70% w/w.

13. The method of claim 1, wherein the pharmaceutical composition further comprises a preservative present in an amount of no more than about 1% w/w, wherein the preservative is selected from the group consisting of methylparaben, propylparaben, and mixtures thereof.

14. The method of claim 13, wherein the preservative is present in an amount of about 0.2% w/w.

15. The method of claim 1, wherein the compound of formula (II), or a crystalline form thereof, is present in an amount of about 0.40% w/w to about 0.50% w/w, and the sodium bicarbonate is present in an amount of about 0.42% w/w.

16. The method of claim 15, wherein the pharmaceutical composition further comprises a taste-masking agent.

17. A method for treating Aurora A kinase mediated cancer, comprising the administration of a therapeutically effective amount of a liquid pharmaceutical composition comprising a sodium salt of formula (II):

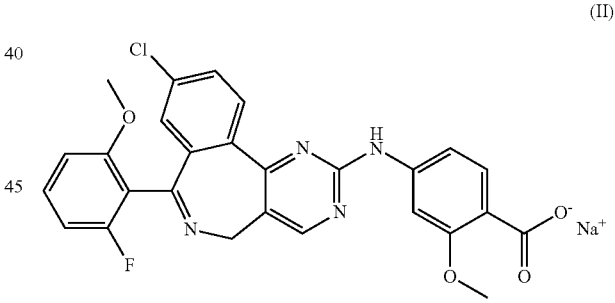

(II)

or a crystalline form thereof, wherein the pharmaceutical composition comprises the sodium salt of formula (II) in an amount of about 0.40% w/w to about 0.50% w/w; sodium bicarbonate in an amount of about 0.42% w/w; acesulfame potassium; a flavoring agent; and solvent in an amount of about 97%, or about 98%, or about 99% w/w, wherein the solvent is a mixture of propylene glycol, glycerin, PEG400, and purified water, and wherein the solvent contains less than about 50% purified water, and the composition contains at least about 15% w/w propylene glycol and at least about 15% w/w PEG400.

18. The method of claim 17, wherein the cancer is colorectal cancer, lung cancer, ovarian cancer, breast cancer, gastric cancer, prostate cancer, pancreatic cancer, neuroblastoma, or acute lymphoblastic leukemia.

19. A method for treating Aurora A kinase mediated cancer, comprising the administration of a therapeutically effective amount of a liquid pharmaceutical composition comprising a sodium salt of formula (II):

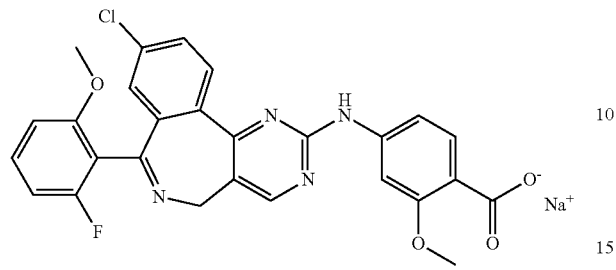

(II)

or a crystalline form thereof, wherein the pharmaceutical composition comprises the sodium salt of formula (II) in an amount of about 0.40% w/w to about 0.50% w/w: sodium bicarbonate in an amount of about 0.42% w/w; sorbitol; and solvent in an amount of about 68%, or about 69%, or about 70% w/w, wherein the solvent is a mixture of propylene glycol, PEG400, and purified water, and wherein the solvent contains less than about 50% purified water, and the composition contains at least about 15% w/w propylene glycol and at least about 15% w/w PEG400.

20. The method of claim 19, wherein the cancer is colorectal cancer, lung cancer, ovarian cancer, breast cancer, gastric cancer, prostate cancer, pancreatic cancer, neuroblastoma, or acute lymphoblastic leukemia.

* * * * *